United States Patent [19]

Yu et al.

[11] 4,053,630

[45] Oct. 11, 1977

[54] TREATMENT OF BODY ODOR AND DISTURBED KERATINIZATION

[76] Inventors: Ruey J. Yu, 4400 Dexter St., Philadelphia, Pa. 19128; Eugene J. Van Scott, 1138 Sewell Lane, Rydal, Pa. 19046

[21] Appl. No.: 703,188

[22] Filed: July 7, 1976

[51] Int. Cl.$^2$ .......................................... A61K 31/315
[52] U.S. Cl. ................................... 424/289; 424/65; 424/67; 424/68; 424/294; 424/295; 424/319
[58] Field of Search ..................... 424/65, 67, 68, 289, 424/294, 295, 319

[56] References Cited

PUBLICATIONS

Johnston, Chemical Abstracts 78:80629k (1973).
Van Herreveld et al., Chemical Abstracts 76:2241x (1972).
McCully, Chemical Abstracts 75:73327v (1971).
Tsuchiya et al., Chemical Abstracts 73:23707g (1970).
Tanaka et al., Chemical Abstracts 70:68709p, (1969).
Zbigniew et al., Chemical Abstracts 68:48024s, (1968).

*Primary Examiner*—Norman A. Drezin
*Attorney, Agent, or Firm*—LeBlanc & Shur

[57] ABSTRACT

A treatment to prevent the symptoms of skin conditions characterized by an offensive odor of the body, and a treatment to alleviate the symptoms of diseases characterized by defects of keratinization consisting of the topical application of a solution, lotion, cream, ointment, powder, stick or spray containing cysteic acid, cysteinesulfinic acid, homocysteic acid or their metal chelates are disclosed. The metal chelates include molecular complexes of cysteic acid or its analogue and metal ions such as ferric, cupric, zinc and aluminum ions. The efficacious compositions may include the active ingredients present in a total amount of from 1 to 30 percent, and preferably from 2 to 10 percent by weight. In a prophylactic treatment topical application to skin areas of axilla, crotch (inguinalperineum) and feet has been found to prevent the formation of malodor. In a therapeutic treatment for the disturbed keratinization topical application to affected areas has been found to achieve a complete remission of ichthyosis, dandruff and acne.

11 Claims, No Drawings

TREATMENT OF BODY ODOR AND DISTURBED KERATINIZATION

BACKGROUND OF THE INVENTION

This invention relates to a prophylactic treatment for skin conditions characterized by malodor of the body, and to a therapeutic treatment for diseases characterized by defective keratinization including ichthyosis, dandruff and acne, and specifically to the compounds and their chelation derivatives which have been found to be effective, when topically applied, to achieve a complete absence of malodor from the treated body areas, and to resolve the skin lesions associated with the above diseases in humans.

MALODOR

Body odors of man are in large measure consequent to perspiration of the skin. Anatomically there are two types of sweat glands in human skin, namely eccrine glands and apocrine glands. Eccrine glands, also called true sweat glands, occur all over the body surface except on the lips and certain portions of the sex organs. Since these glands secrete only water and certain water soluble simple substances such as sodium chloride and lactic acid their secretions do not directly give rise to objectionable odors.

Apocrine glands occur primarily in the axilla, anogenital region, mammary areola and ear canal but also irregularly on parts of the trunk, scalp and face. In general the apocrine duct opens into the upper end of the hair follicle although it may occasionally open directly onto the skin surface. In contrast to the eccrine gland, which produces a clear liquid, the apocrine gland secretes a milky fluid that has a pH range of 5 to 6.5 and consists of lipids, proteins and carbohydrates. Although fresh apocrine secretion does not have an objectionable odor, it is known to undergo degradation by both chemical and microbial attack, the products of which account for offensive odors. Chemical substances identified as contributing to this unpleasant odor include lower organic acids such as butanoic, isopentanoic, hexanoic and octanoic acids; mercaptans; indoles; amines; hydrogen sulfide; ammonia; and phosphine. Although gram-positive bacteria, thriving on substances found on the moist skin surface, appear to be responsible for the production of malodor, the precise mechanisms of odor production are still unclear.

Many deodorant or antiperspirant products on the market today are salts of aluminum or zinc. The aluminum salts include aluminum chloride, aluminum chlorhydroxide, aluminum sulfate, aluminum potassium sulfate and aluminum phenolsulfonate. The zinc salts comprise zinc oxide, zinc peroxide, zinc stearate and zinc phenolsulfonate. Other substances used in such products include quaternary ammonium compounds and a few antibiotics such as aureomycin, thyrothricin and neomycin.

Although long-term use of aluminum or zinc salts as underarm deodorants present no major problem in toxicity, those compounds do frequently cause irritations, burnings, itching and other uncomfortable sensations. Many people stop using existing underarm deodorants available on the market today because of persistent itching or burning after use.

Development of other efficacious anti-odorant substances, preferably of physiologic origin, which do not cause irritation, itching or uncomfortable sansation when applied to the skin is therefore desirable.

ICHTHYOSIS

The term ichthyosis alludes to a fish scale-like appearance of the human skin. In dermatology, ichthyotic conditions are classified as ichthyosiform dermatoses which are hereditary disorders wherein excessive amounts of scale accumulates on the skin surface.

There are four types of ichthyosis known. Each type has a characteristic genetic mode of inheritance, and each type exhibits different clinical and cellular kinetic characteristics. The four types known are identified as follows:

1. *Ichthyosis vulgaris,* characterized by a "dry skin" appearance, is first detected during the early years of childhood. Small, fine scales with a "pasted-on" appearance are found most prominently on the trunk and upper extremities. Larger, more adherent scales are present on the legs.

2. *Lamellar ichthyosis* is marked by almost universal scaling, and is present at birth, persisting into adulthood. The scales are large, 0.5 to 1.5 centimeters in diameter, gray-brown in color, and, frequently, adherent at their centers with slightly raised edges.

3. *Epidermolytic hyperkeratosis* is characterized by a thick, scaly mantle which covers the body at birth. The mantle is shed almost immediately and leaves a raw body surface. The skin then gradually becomes dry and scaly again and assumes the changes characteristic of this disorder.

4. *X-linked ichthysis* affects primarily males and is characterized by scales prominent on the trunk, neck and extremities.

Conventional treatments for ichthyotic conditions primarily involve the topical application of hydrating emollients. In addition, ointments containing salicylic acid or vitamin A acid have been used. Prior treatments, however, have not been universally successful, and have been, in many cases, unable to promote healing to cause a complete remission of the symptoms. Because the mechanism whereby the genetic mode of inheritance results in an ichthyotic condition is not known, treatment has at best resulted in a temporary remission or healing of the scaly lesion.

As described in U.S. Pat. No. 3,879,537, issued on Apr. 22, 1975 entitled TREATMENT OF ICHTHYOSIFORM DERMATOSES, we discovered that certain lower aliphatic compounds having two to about six carbon atoms and preferably having $\alpha$-carbon functionality were effective against ichthyotic conditions in humans, and to cause a remission thereof and healing of the lesions. More specifically the compounds found to be effective were glycolic acid, citric acid, lactic acid, malic acid, tartronic acid, tartaric acid, glucuronic acid, pyruvic acid, methyl pyruvate, ethyl pyruvate, 2-hydroxyisobutyric acid and 3-hydroxybutyric acid.

OTHER SKIN DISORDERS

Other disease conditions characterized by defects in keratinization are relatively common and many different treatments have been prescribed in the past with varying degrees of effectiveness. In each of these disease conditions the process whereby the epidermal cells mature and form a surface layer (stratum corneum) is defective. Therefore the signs and symptoms of diseases associated with defective keratinization are an overproduction of cells and/or their retention in the stratum corneum for abnormally prolonged periods. More specifically these skin diseases include dandruff, acne, psoriasis, palmar and plantar hyperkeratosis.

In our patent application Ser. No. 445,231 filed Feb. 25, 1974 now U.S. Pat. No. 3,920,835, issued Nov. 18, 1975 and entitled TREATMENT OF DISTURBED KERATINIZATION, a treatment was described for dandruff, acne and palmar and plantar hyperkeratosis. In this disclosure topical application of certain α-hydroxy acids and related compounds to affected areas are reported to achieve a complete remission of dandruff, acne and palmar and plantar kyperkeratosis. More specifically the compounds indicated to be effective were glycolic acid, citric acid, lactic acid, malic acid, tartronic acid, tartaric acid, glucuronic acid, pyruvic acid, methyl pyruvate, ethyl pyruvate, 2-hydroxyisobutyric acid and 3-hydroxybutyric acid.

SUMMARY OF THE INVENTION

It has been discovered that skin conditions characterized by malodor may be successfully prevented by the application of cysteic acid, cysteinesulfinic acid, homocysteic acid or their metal chelates. It has been discovered that ichthyotic conditions may also be successfully treated with cysteic acid, homocysteic acid or cysteinesulfinic acid. Finally, it has been discovered that the above skin disorders, such as dandruff, acne, psoriasis, palmar and plantar hyperkeratosis, may also be successfully treated with cysteic acid, homocysteic acid or cysteinesulfinic acid.

DETAILED DESCRIPTION OF THE INVENTION

Cysteic acid, also called β-sulfoalanine or α-amino-β-sulfopropionic acid, available as the L or DL form with a molecular weight of 169 ($C_3H_7NO_5S$), is an oxidation product of the sulfur-containing amino acids, cysteine or cystine. Cysteic acid, a nontoxic and nonallergenic physiologic compound, has recently been found in human and animal blood, especially in the platelets and leukocytes; in the brain, both in the gray and white matter; and in the teeth. This compound is also found in human hair after treatment with an oxidizing agent. Cysteic acid occurs normally in the outer part of the sheep's fleece where the wool is exposed to light and weather.

L-Cysteinesulfinic acid, $C_3H_7NO_4S$, molecular weight of 153, which has one oxygen atom less than cysteic acid, is an intermediate oxidation product from cysteine or cystine. It is also a nontoxic compound.

Homocysteic acid, $C_4H_9NO_5S$, molecular weight of 183, commercially available as its DL form, is an oxidation product of the sulfur-containing amino acid, homocysteine or homocystine, which is found in the liver of mammals as an intermediate in the metabolic conversion of methionine to cysteine.

PREPARATION OF THE THERAPEUTIC COMPOSITION

To prepare a therapeutic composition, L or DL-cysteic acid, L-cysteine sulfinic acid or DL-homocysteic acid is first dissolved in water. If a metal chelate of cysteic acid or its analogues to be used, metallic compounds, such as ferric chloride, copper sulfate, copper carbonate zinc sulfate, zinc oxide, zinc chloride, aluminum chlorohydrate or aluminum zinc sulfate, may be added to chelate the cysteic acid or its analogues in solution. The solution thus prepared may be admixed in a conventional manner with any commonly available lotion, cream or ointment.

The concentration of cysteic acid or its analogues ranges from 1 to 30% by weight of the total therapeutic composition. The preferred concentration range, however, is from 2 to 10%. When a metal chelate of cysteic acid or its analogues is used as an active ingredient, the concentration of the metallic salt or other metallic compound ranges from 0.1% to 5% by weight of the total composition. The preferred concentration range of the metallic compound, however, is from 0.1 to 2% by weight.

Although on the molecular level one mole of metal ion such as cupric ion may form a copper chelate with one or more than one mole of cysteic acid or its analogues it is much easier and more practical to prepare the therapeutic composition on a percentage basis, especially when the composition is intended for topical use.

The water used to dissolve cysteic acid or its analogues according to this invention may range in concentration of from 10 to 80% by weight of the total composition. The preferred water concentration, however, is 40 to 80% by weight.

When a therapeutic composition is prepared in a solution form, cysteic acid, its analogues or the metal chelate may be dissolved directly in a mixture of water and ethanol in a preferred volume ratio of 70:30. The ratio of each vehicle may vary; however, the preferred concentration of ethanol should not exceed 80% by weight of the total solvent. Propylene glycol may also be added to the above solution. In this instance, the preferred concentrations of water, ethanol and propylene glycol may be 60, 30 and 10% by weight respectively. Again, the ratio of each vehicle may vary; however, the preferred concentration of ethanol and propylene glycol should not exceed 80% and 30% by weight, respectively.

A therapeutic composition of cysteic acid or its analogues may also be prepared in a powder form. Cysteic acid or its analogues may be first ball-milled to a fine powder and then admixed with a talc. The concentration of cysteic acid or its analogues may range from 2 to 30% by weight of the composition; the preferred concentration however is 5 to 10% by weight.

It has been found that the therapeutic compositions of this invention, prepared as above, may be stored in plastic or glass bottles or jars at room temperatures for extended periods of time without change in therapeutic efficaciousness.

Therapeutic compositions containing cysteic acid, its analogues or the metal chelates may also be prepared in a stick form or in a conventionally available spray can, using conventional techniques.

The following are illustrative examples of formulations of compositions according to this invention. Although the examples utilize only selected members of the above-listed compounds, useful according to this invention, it should be understood that the following examples are illustrative and not limiting. Therefore, any of the above compounds may be substituted according to the teachings of this invention and the following formulations:

EXAMPLE 1

L-Cysteic acid, 2 grams, was dissolved in 50 ml of water. Ethanol, 50 ml, was then added to make a 2% concentration of the acid.

EXAMPLE 2

Example 1 was repeated, except that L-cysteic acid was replaced by L-cysteinesulfinic acid.

EXAMPLE 3

Example 1 was repeated, except that L-cysteic acid was replaced by DL-homocysteic acid.

EXAMPLE 4

L-Cysteic acid, 5 grams, was dissolved in 50 ml of water. The solution was admixed with 40 ml of ethanol and 10 ml of propylene glycol to make a composition containing 5% by weight of the acid.

EXAMPLE 5

Example 4 was repeated except that L-cysteic acid was replaced by L-cysteinesulfinic acid.

EXAMPLE 6

Example 4 was repeated except that L-cysteic acid was replaced by DL-homocysteic acid.

EXAMPLE 7

L-Cysteic acid, 5 grams, was dissolved in 10 ml of water and the solution was admixed with 85 grams of hydrophilic ointment, USP until a uniform consistency resulted.

EXAMPLE 8

Example 7 was repeated, except that L-cysteic acid was replaced by L-cysteinesulfinic acid.

EXAMPLE 9

Example 7 was repeated, except that L-cysteic acid was replaced by DL-homocysteic acid.

EXAMPLE 10

L-Cysteic acid ($C_3H_7NO_5S \cdot H_2O$) 5,6g (30 m moles) was dissolved in 70 ml of water, and ferric chloride ($FeCl_3 \cdot 6H_2O$), 2.7g was added to the solution with constant stirring until a clear orange solution formed. Ethanol, 20 ml, and propylene glycol 10 ml, were added to the solution to make a composition of cysteic acid chelated with ferric ion.

EXAMPLE 11

L-Cysteic acid ($C_3H_7NO_5S \cdot H_2O$), 1.87g (10 m mole) was dissolved in 40 ml of water. Cupric sulfate ($CuSO_4 - 5H_2O$), 0.25g (1 m mole) was then added to the solution with stirring until a clear blue solution formed. Ethanol, 50 ml, and propylene glycol, 10 ml, were added to make a composition of the copper chelate of cysteic acid.

EXAMPLE 12

L-Cysteic acid, 2 grams, was dissolved in 80 ml of water. Cupric carbonate, 0.5 gram, was added to the solution with stirring until a clear blue solution formed. Ethanol, 10 ml, and propylene glycol, 10 ml, were added to the solution to make a composition of the copper chelate of cysteic acid.

EXAMPLE 13

Example 12 was repeated, except that L-cysteic acid was replaced by L-cysteinesulfinic acid.

EXAMPLE 14

Example 12 was repeated, except that L-cysteic acid was replaced by DL-homocysteic acid.

EXAMPLE 15

L-Cysteic acid, 5 grams, was dissolved in 50 ml of water. Zinc oxide, 1 gram, was then added to the solution with stirring until a clear solution formed. Ethanol, 40 ml, and propylene glycol, 10 ml, were added to make a composition of the zinc chelate of cysteic acid.

EXAMPLE 16

Example 15 was repeated, except that L-cysteic acid was replaced by L-cysteinesulfinic acid.

EXAMPLE 17

Example 15 was repeated, except that L-cysteic acid was replaced by DL-homocysteic acid.

EXAMPLE 18

L-Cysteic acid, 5 grams, was dissolved in 70 ml of water. Zinc chloride, 2 grams, was then added to the solution with stirring. Ethanol, 20 ml, and propylene glycol, 10 ml, were added to make a composition of the zinc chelate of cysteic acid.

EXAMPLE 19

Example 18 was repeated, except that L-cysteic acid was replaced by L-cysteinesulfinic acid.

EXAMPLE 20

Example 18 was repeated, except that L-cysteic acid was replaced by DL-homocysteic acid.

EXAMPLE 21

L-Cysteic acid, 2 grams, was dissolved in 70 ml of water. Aluminum chloride ($AlCl_3 \cdot 6H_2O$), was added to the solution with stirring. Ethanol, 20 ml, and propylene glycol, 10 ml, were added to make a composition of the aluminum chelate of cysteic acid.

EXAMPLE 22

Example 21 was repeated, except that L-cysteic acid was replaced by L-cysteinesulfinic acid.

EXAMPLE 23

Example 21 was repeated, except that L-cysteic acid was replaced by DL-homocysteic acid.

EXAMPLE 24

L-Cysteic acid, 2 grams, was dissolved in 40 mls of water. Aluminum zinc sulfate, 1 gram, was then added to the soltuion with stirring. Ethanol, 50 ml, and propylene glycol, 10 ml, were added to make a composition of the aluminum zinc chelate of cysteic acid.

EXAMPLE 25

Example 24 was repeated, except that L-cysteic acid was replaced by L-cysteinesulfinic acid.

EXAMPLE 26

Example 24 was repeated, except that L-cysteic acid was replaced by DL-homocysteic acid.

EXAMPLE 27

Finely powdered L-cysteic acid, 10 grams, was mixed with 90 grams of fine talc until a uniform powder mixture was obtained. The therapeutic composition of this formulation may be stored in a powder can with holes in the cap at room temperature for extended periods of time without change in therapeutic effectiveness caused by humidity changes in the air.

EXAMPLE 28

Example 27 was repeated, except that L-cysteic acid was replaced by L-cysteinesulfinic acid.

EXAMPLE 29

Example 27 was repeated, except that L-cysteic acid was replaced by DL-homocysteic acid.

EXAMPLE 30

L-Cysteic acid, 5 grams, was dissolved in 45ml of water. Triethanolamine lauryl sulfate, 50 ml, was added to make a composition of 5% active ingredient in a shampoo preparation.

EXAMPLE 31

Example 30 was repeated, except that L-cysteic acid was replaced by L-cysteinesulfinic acid.

EXAMPLE 32

Example 30 was repeated, except that L-cysteic acid was replaced by DL-homocysteic acid.

EXAMPLE 33

L-Cysteic acid, 2 grams, was dissolved in 20 ml of water. N-Methyldiethanolamine, 1.2 ml, was added to partially neutralize the acidity of the mixture. Ethanol, 50 ml, and sufficient water were added to make 2% active ingredient in a composition of 50% alcoholic aqueous solution.

EXAMPLE 34

Example 33 was repeated, except that L-cycteic acid was replaced by L-cysteinesulfinic acid.

EXAMPLE 35

Example 33 was repeated, except that L-cysteic acid was replaced by DL-homocysteic acid.

EXAMPLE 36

| Part A: | Polyoxyethylene sorbitan monooleate (Tween 80) | 5 grams |
| --- | --- | --- |
|  | Cetyl alcohol | 23 grams |
|  | Cholesterol | 0.4 gram |
|  | Squalene | 0.2 gram |
| Part B: | Water | 56 ml |
|  | Propylene glycol | 10 ml |
|  | L-Cysteic acid | 5 grams |
|  | Ethanolamine | 1 ml |

Part A was heated to 70° C and Part B was heated to 72° C.
Part B was slowly added to Part A with agitation. Agitation was continued until the mixture was congealed. The water-washable cream thus prepared consisted of 5% active ingredient.

TEST RESULTS

Antiodorant Effectiveness

The therapeutic compositions of the aforementioned preparations were tested topically on more than 27 human volunteers as well as on patients who had skin disease emanating foul odors and who sought treatment of these conditions. Most of these subjects could not use existing market products of antiperspirants or deodorants because those products either irritated or caused itching of their skin, especially in the underarm areas and other areas where skin surfaces are in apposition.

The subjects were instructed to take a shower in the morning using ordinarily available soap to clean the body surfaces. After the skin was dried the test composition of the present invention was topically applied to one underarm area only. The vehicle control was topically applied to the other underarm area. Both underarm areas were monitored by the subject and at least two other persons approximately every 8 hours to determine whether the test composition had substantial antiodorant effects as compared to the vehicle alone on the control site. Presence or absence of odor, determined by smell, was the criteria for ineffectiveness or effectiveness, respectively.

After the subject developed an offensive odor on the control side, the degree of effectiveness of the test composition on the other side was classified as follows: (a) no effect (no difference from the control): (b) moderate effectiveness (only a trace of malodor): and (c) complete effectiveness (no offensive odor could be detected by at least 3 examiners during a 24-hour test period). Both moderate and complete effectiveness implied that the effectiveness lasted for at least 24 hours. After the test composition had been found to be effective as an antiodorant on the left side of the underarm the right side of the underarm was then treated in the same way to ascertain that the antiodorant composition gave the same consistent result.

The test results of the present invention showed the following:

1. Cysteic acid, cysteinesulfinic acid, homocysteic acid and their metal chelates exhibited no signs of irritation, burning or itching of the skin.
2. Cysteic acid, its analogues and metal chelates thereof had no primary antiperspirant effect.
3. Cysteic acid, its analogues and metal chelates thereof had a moderate to complete effectiveness as antiodorants. Among those compositions, copper chelate (Example 11) and aluminum zinc chelate (Examples 24 – 26) gave a complete effectiveness as topical antiodorants on all the human subjects tested.

Antiodorant effectiveness of the therapeutic composition on foot malodor was determined as follows: The test subject was instructed to spread loosely the powder of the therapeutic composition (Example 27) on and around the left sole before wearing a sock in the morning. The talc alone powder was spread on the right sole as a control. Both soles were checked 8 hours later to determine whether the test composition had any substantial antiodorant effect. The degree of effectiveness as an antiodorant for the foot was classified in the same way as described above for the underarm. It has been found that cysteic acid, its analogues and the metal chelates thereof had a moderate to complete effectiveness as antiodorants for the foot.

TREATMENT OF ICHTHYOSIS

Six patients having ichthyosis were treated with a composition as follows:

Patients with ichthyosis were instructed first to wet the body by taking a shower and then applying a thin film of 5% ointment formulated according to Example 7 above to the lesions. Twice daily topical application was continued for several weeks. Generally, the affected skin became less scaly and felt smoother after about a week of topical treatment. The scaly lesions ordinarily were substantially clear after two weeks of treatment. The sites of lesions, devoid of any scales, usually reached an improved state comparable to normal appearing skin within 2 to 4 weeks after initial treatment.

Once a normal appearing skin was restored, it remained improved for from several weeks to several months, varying from patient to patient, without further application of the ointment. It is, however, necessary to continue the application of the ointment in order to maintain the skin free from recurrence of the overt disease.

In all the patients tested cysteic acid and homocysteic acid (and their metal chelates) were both equally effective in alleviating ichthyotic disorder to normal appearing skin within two weeks after initial treatment.

TREATMENT OF DANDRUFF

Twelve patients with severe dandruff problems were instructed first to shampoo their scalp and hair with a shampoo formulation as described in Examples 30 and 32. After shampoo the patients were advised to rub into the scalp a medication as described in Examples 4 – 6. The above treatment was carried out twice weekly. The shampoo and the after shampoo formulations prevented all signs of dandruff, i.e. formation of scales on the scalp in all twelve patients. Relief was observed within about a week in each case and normal skin condition was observed to be maintained at least one to two weeks after treatment was terminated.

TREATMENT OF ACNE

Twelve patients with acne were instructed to apply topically first a solution as described in Examples 4 – 6 and then a cream prepared according to Example 36 twice daily on the skin of the face for four weeks. Eleven of the twelve patients tested showed substantial reduction in the number of acne lesions after 4 weeks of topical treatment.

In summary, it has been discovered that cysteic acid, cysteinesulfinic acid, homocysteic acid and their metal chelates are effective as antiodorants in preventing the formation of an offensive odor of the body. It has also been discovered that these compounds are therapeutically effective against skin disorders characterized by hyperkeratinization, such as ichthyosis, dandruff and acne.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by U.S. Letters Patent is:

1. A method for treating acne, dandruff and ichthyotic skin conditions, said method comprising topically applying to the involved skin are as a symptom alleviating and therapeutically effective amount of a medicinal composition containing from about 1 to about 30 percent by weight of at least one compound selected from the group consisting of cysteic acid, cysteinesulfinic acid and homocysteic acids and chelates of said compound with at least one metallic compound selected from the group consisting of ferric chloride, copper sulfate, copper carbonate, zinc sulfate, zinc oxide, zinc chloride, aluminum chlorohydrate and aluminum zinc sulfate.

2. Method of claim 1, wherein said compound is present in an amount of from about 2 to about 10 percent by weight.

3. Method of claim 1, wherein said compound is a metal chelate, and said composition contains from about 0.1 to about 5% by weight of metal ion, based on the weight of the total composition.

4. Method of claim 1, wherein said medicinal composition is a liquid solution containing from 10 to about 80 percent by weight of water, based on the weight of the total composition.

5. Method of claim 4, wherein said solution also contains ethanol, in an amount of no greater than 80 percent by weight of the amount of ethanol and water combined.

6. Method of claim 1, wherein said medicinal composition is in powder form, and said powder contains from 2 to 30 percent by weight of said compound.

7. Method of claim 6, wherein said powder contains from 5 to 10 percent by weight of the composition of said compound.

8. Method of claim 1 wherein said skin condition exhibits malodor as a symptom thereof and said method comprises topically applying a malodor reducing, effective amount of said composition to involved skin areas.

9. Method of claim 1 wherein said skin condition is the disease ichthyosis.

10. Method of claim 1 wherein said skin condition exhibits dandruff as a symptom thereof and said method comprises topically applying a dandruff reducing, effective amount of said composition to involved skin areas.

11. Method of claim 1 wherein said skin condition is the disease acne.

* * * * *